United States Patent [19]

Meul

[11] Patent Number: 4,906,759

[45] Date of Patent: Mar. 6, 1990

[54] PROCESS FOR THE PRODUCTION OF 4-ALKOXY-2(5H) THIOPHENONES

[75] Inventor: Thomas Meul, Visp, Switzerland

[73] Assignee: Lonza Ltd., Gampel/Valais, Switzerland

[21] Appl. No.: 97,109

[22] Filed: Sep. 16, 1987

[30] Foreign Application Priority Data

Sep. 24, 1986 [CH] Switzerland .......................... 3827/86

[51] Int. Cl.$^4$ ................................. C07D 333/34
[52] U.S. Cl. ................................................ 549/62
[58] Field of Search ........................................ 549/62

[56] References Cited

U.S. PATENT DOCUMENTS

| | | | |
|---|---|---|---|
| 2,535,010 | 12/1950 | Croxall | 260/484 |
| 2,784,191 | 3/1957 | Fischer et al. | 260/294.7 |
| 4,118,396 | 10/1978 | Pifferi et al. | 260/326.43 |
| 4,124,594 | 11/1978 | Monguzzi et al. | 260/326.43 |
| 4,173,569 | 11/1979 | Banfi et al. | 260/326.43 |

FOREIGN PATENT DOCUMENTS

| | | |
|---|---|---|
| 0028709 | 5/1981 | European Pat. Off. . |
| 0060808 | 11/1982 | European Pat. Off. . |
| 192255 | 8/1986 | European Pat. Off. . |
| 850007 | 9/1952 | Fed. Rep. of Germany . |
| 183756 | 11/1982 | Japan . |
| 840658 | 7/1960 | United Kingdom . |
| 1266092 | 3/1972 | United Kingdom . |
| 1266093 | 3/1972 | United Kingdom . |
| 1299298 | 12/1972 | United Kingdom . |
| 1299299 | 12/1972 | United Kingdom . |
| 1362143 | 7/1974 | United Kingdom . |
| 1362144 | 7/1974 | United Kingdom . |

OTHER PUBLICATIONS

J. Z. Mortensen et al., Tetrahedron 27, 3839 (1971).
Chem. Abst., vol. 43 (1949), p. 2238.
Chem. Abst., vol. 78 (1973), 29615 A.
English language translation of German Pat. No. 850,007.
Chemical Abstracts 105:226341.
Chemical Abstracts, vol. 52, 11124g.
Lowe, J. Chem. Soc., Perkin Trans. I, 1973, 2907–2910.
Sidgwick, "The Organic Chemistry of Nitrogen", 3rd Ed., Oxford (1966), p. 637.
Ho et al., "Cleavage of Ester and Ether with Iodotrimethylsilane", Angewandte Chemie, vol. 15, No. 12, (12/76), pp. 774 and 775.
Cram et al., J. Am. Chem. Soc., 1963, 85, pp. 1430–1437.
Koehler, Dissertation Bayreuth, (1985).
MacKenzie et al., J.O.C.S., 20, No. 12, (1955), pp. 1695 and 1696.
G. Pifferi et al., Il Farmaco, Ed. Sc., (1977), 32, 602–613.
Katsuri et al., Bull. Chem. Soc. Japan, vol. 49, (11) (1976), pp. 3287–3290.
Chemical Reviews, vol. 86, No. 2, (Apr. 1986), pp. 245 and 246.

*Primary Examiner*—Alan Siegel
*Attorney, Agent, or Firm*—Fisher, Christen & Sabol

[57] ABSTRACT

Process for the production of 4-alkoxy-2(5H) thiophenones, which are suitable as intermediate products, i.e., for the production of highly pure thiotetronic acid.

16 Claims, No Drawings

PROCESS FOR THE PRODUCTION OF 4-ALKOXY-2(5H) THIOPHENONES

BACKGROUND OF THE INVENTION

1. Field of the Invention

The invention relates to the production of 4-alkoxy-2(5H) thiophenones.

2. Background Art

Up to now advantageous processes have been lacking for producing thiotetronic acid, especially thiotetronic acid in highly pure form, in a good yield.

From E. Benary, Chem. Berichte 46, 2103 (1913), it is known to produce thiotetronic acid, starting from acetylthioglycoyl chloride, by reaction with sodium malonic ester and subsequent ring closure and water treatment. D. B. Macierewicz, Rocz. Chem. 47, 1735 (1973), duplicated the reaction of E. Benary and in doing so obtained thiotetronic acid in a yield of 30.3 percent, in relation to the acetylthioglycoyl chloride used.

The synthesis of J. Z. Mortensen et al., Tetrahedron 27, 3839 (1971), shows another possibility. Starting from 2,4-dibromothiophene, the thiotetronic acid is obtained in a yield of 46.2 percent through three steps by reaction with butyl lithium and tert-butyl perbenzoate.

Moreover, it is known from European Patent Application No. 0189097 and the corresponding U.S. application Ser. No. 818,766, filed on Jan. 14, 1986, which was refiled on July 23, 1987, as U.S. application Ser. No. 76,855, to produce thiotetronic acid by the reaction of chloroacetoacetic acid chloride with H$_2$S in the presence of trimethylamine. A disadvantage of such process is that the thiotetronic acid can be produced only by an expensive extraction with inadequate quality (content 88 percent). In addition, working with gaseous H$_2$S in regard to an industrial process is not without problems. The pertinent parts of U.S. Ser. No. 76,855, filed on July 23, 1987, for "Process For The Production Of Thiotetronic Acid", which is a continuation of U.S. Ser. No. 818,766, filed on Jan. 14, 1986, are incorporated herein by reference.

For the production of a better thiotetronic acid quality, a process is known from European Patent Application No. 0189096 and the corresponding U.S. application Ser. No. 818,747, filed on Jan. 14, 1986, which is distinguished by the reaction of 4-chloro-4-chloromethyloxetan-2-one with hydrogen sulfide in the presence of an amine directly to the thiotetronic acid, or in a second variant by the reaction of the unisolated thiotetronic acid with ketene to 2,4-diacetoxythiophene, which for its part is reacted with a mineral acid to thiotetronic acid. A disadvantage of such process is that it is started using an deduct which is not available on a large industrial scale but which must be produced in a separate synthesis step. In addition, a pure thiotetronic acid is possible according to the first variant only after a chromatographic purification and according to the second variant only by the roundabout way of the production of the easily purified 2,4-diacetoxythiophene. Also such process, because of the use of H$_2$S in the industrial framework, must be evaluated as having problems associated therewith. The pertinent parts of U.S. Ser. No. 818,747, filed on Jan. 14, 1986, for "Process For The Production Of Thiotetronic Acid", are incorporated herein by reference.

BROAD DESCRIPTION OF THE INVENTION

The main object of the invention is to provide a process which is not subject to the above-described drawbacks or disadvantages. Other objects and advantages of the invention are set out herein or are obvious here from to one skilled in the art.

An industrially feasible process was unexpectedly found whereby, without the use of the problematic hydrogen sulfide, starting from a haloacetoacetic acid alkyl ester, available on a large industrial scale, by reaction with orthoformic acid trialkyl ester and further reaction with 3-alkoxy-4-halo-2E-butenoic acid alkyl ester according to one of two reaction schemes one can produce 4-alkoxy-2(5H) thiophenones of the formula:

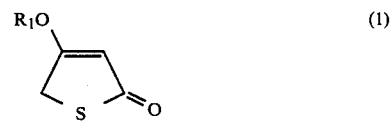

wherein R$_1$ is straight-chain or branched alkyl with 1 to 4 carbon atoms, which are starting products for further thiotetronic acid derivatives or in an excellent way are suitable as an intermediate step for the securing of highly pure thiotetronic acid.

Suitably, the procedure is so conducted that in a first step in a known way, e.g., according to Swiss Patent Application No. 4119/85, U.S. application No. 907,012, filed on Sept. 15, 1986, U.S. application No. 931,806, filed on Nov. 18, 1986, and U.S. application No. 931,849, filed on Nov. 18, 1986, from 4-haloacetoacetic acid alkyl ester by reaction with an orthoformic acid trialkyl ester in the presence of an acid a 3-alkoxy-4-halo-2E-butenoic acid alkyl ester of the formula:

is produced wherein R$_1$ and R$_2$ are straight-chain or branched alkyls with 1 to 4 carbon atoms, and Hal is chlorine or bromine. The pertinent parts of U.S. Ser. No. 907,012, filed on Sept. 15, 1986, for "4-Alkoxy-3-pyrrolin-2-on-1-yl Acetic Acid Alkyl Esters And Their Production", U.S. Ser. No. 931,806, filed on Nov. 18, 1986, for "4-Alkoxy-3-pyrrolin-2-on-1-yl Acetic Acid Alkyl Esters And Their Production", and U.S. Ser. No. 931,849, filed on Nov. 18, 1986, for "4-Alkoxy-3-pyrrol n-2-on-1-yl Acetic Acid Alkyl Esters And Their Production", are incorporated herein. The 3-alkoxy-4-halo-2E-butenoic acid alkyl ester after that is reacted according to the invention by either of two schemes. In the first scheme, the ester of formula (2) is reacted with an alkali thioacetate to 3-alkoxy-4-thioacetoxy-2E-butenoic acid alkyl ester and is further reacted, after isolation of it, with an alkali hydroxide to 4-alkoxy-2(5H) thiophene. In the second scheme, the ester of formula (2) is converted directly with an alkali hydrogen sulfide into 4-alkoxy-2(5H) thiophenone.

If the procedure follows the two-step process (scheme), the alkali thioacetates are generated with thioacetic acid, advantageously immediately before reaction, with the 3-alkoxy-4-halo-2E-butenoic acid alkyl ester, suitably by reaction of an alkali alcoholate, which for its part was produced in a known way from the respective alkali metal and the corresponding alcohol. Preferably sodium thioacetate is used as alkali thioacetate, which correspondingly is produced from a sodium alcoholate, preferably sodium methylate, and thioacetic acid. The alkali thioacetate solution can then be mixed, suitably at a temperature between 0° and 30° C., with the corresponding 3-alkoxy-4-halo-2E-butenoic acid alkyl ester. Preferred educts are the 3-alkoxy-4-chloro-2E-butenoic acid methyl esters. The aliphatic alcohol used in the generation of the alkali thioacetate suitably serves as solvent. The preferred aliphatic alcohol is methanol.

After a reaction period of suitably 5 to 10 hours at a temperature suitably between 20° and 50° C., the split off alkali halide can be separated and the corresponding 3-alkoxy-4-thioacetoxy-2E-butenoic acid alkyl ester can be obtained according to a usual method, e.g., by evaporation of the filtrate. The yield in this step is practically quantitative.

The 3-alkoxy-4-thioacetoxy-2E-butenoic acid alkyl esters according to the invention, preferably 3-alkoxy-4-thioacetoxy-2E-butenoic acid methyl ester of the formula:

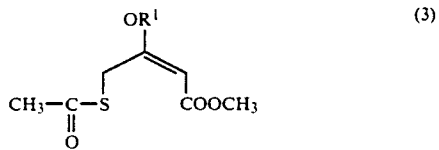

(3)

wherein $R_1$ has the above meaning, are compounds which were not known until now. They can be converted into 4-alkoxy-2(5H) thiophenones in a simple way by reaction with an alkali hydroxide. Sodium and potassium hydroxide are especially suitable as the alkali hydroxide. Advantageously the operation is performed in water as solvent at temperatures of 0° to 40° C. As a rule, the corresponding 4-alkoxy-2(5H) thiophenone already after less than 1 hour can be separated by filtration and optionally be purified by recrystallization.

According to the direct process, the procedure is suitably performed so that the alkali hydrogen sulfide reacted in the lower aliphatic alcohol is present in an excess and is then reacted with 4-alkoxy-3-halo-2E-butenoic acid alkyl ester. Sodium hydrogen sulfide, but most preferably sodium hydrogen sulfide monohydrate, is preferably used as the alkali hydrogen sulfide. The preferred educts are the 3-alkoxy-4-chloro-3E-butenoic acid methyl esters. Suitably an excess of alkali hydrogen sulfide of 10 to 100 percent is used per 1 mol of 3-alkoxy-4-halo-2E-butenoic acid alkyl ester. The alcohol corresponding to the ester radical of the educt is suitably used as the lower aliphatic alcohol. Methanol is preferably used. The reaction temperature is suitably between 20° and 70° C.

After a reaction time of generally 4 to 8 hours it can be worked up in the usual process manner and the corresponding 4-alkoxy-2(5H) thiophenone obtained.

The 4-alkoxy-2(5H) thiophenones can be used as interesting intermediate products for further thiotetronic acid derivatives, particularly since they, including above all 4-methoxy-2(5H) thiophenone, are especially suitable for the production of a highly pure thiotetronic acid.

For this purpose, the corresponding 4-alkoxy-2(5H) thiophenone is suitably dissolved in anhydrous acetic acid. The solution can then be saturated with gaseous hydrochloric acid at a temperature of suitably 20° to 60° C. Suitably, at the temperature selected for the saturation, the reaction mixture is advantageously stirred for 15 to 20 hours.

After the usual working up, suitably by removal of the solvent and washing of the precipitated product, a highly pure thiotetronic acid can be obtained without additional purification with a content of more than 99 percent and yields of more than 93 percent.

The 4-alkoxy-2(5H) thiophenones produced by the invention process form valuable intermediate products for the production of thiotetronic acid derivatives, especially of highly pure thiotetronic acid.

Tetrahedron Letters, Vol. 25, No. 46, (1984) pp. 5243-5246, discloses that the dimethyl homologue compound of thiotetronic acid can be used to make (±)-thiolactomycin, an antibiotic having a broad effective spectrum of activity, and the diethyl homologue compound of thiotetronic acid can be used to make thiotetromycin. Accordingly, the Tetrahedron Letters letter would cause one skilled in the art to recognize the possible use of thiotetronic acid for the production of a thiolactomycin derivative.

The great purity of thiotetronic acid is very important because of its application as an intermediate in the synthesis of (+)biotin.

(+)Biotin is a human vitamin and known as vitamin H. Biotin is also applied as pharmaceutical for treatment of dermatosis or as food additive with grow-enhancing effect for cattle.

DETAILED DESCRIPTION OF THE INVENTION

As used herein, all parts, percentages, ratios and proportions are on a weight basis, unless otherwise stated herein or otherwise obvious herefrom to one skilled in the art. MS means mass spectrometry, and m/z means mass number.

EXAMPLE 1

(a) Production of 4-chloro-3-methoxy-2E-butenoic acid methyl ester 31.0 g (0.2 mol) of 4-chloroacetoacetic acid methyl ester is mixed with 106.0 g (1.0 mol) of orthoformic acid trimethyl ester. 30.0 g of Amberlyst-15 ion exchange resin is added under argon with stirring. Under vigorous formation of gas, the reaction temperature rises to 40° C. After 5 hours of stirring, no educt can any longer be detected in thin-layer chromatography. It is filtered from the ion exchange resin and the residue is distilled in a water jet vacuum. The distillate is mixed with 1.0 g of p-toluene sulfonic acid monohydrate and slowly heated to 150° C., and methanol is distilled off. The reaction mass is then distilled in a water jet vacuum. 24.7 g of a colorless liquid with a boiling point $bp_{12} = 93°$ C. is obtained. Further data concerning the compound is:

NMR (CDCl$_3$) δ=5.16 (s, 1H); 4.67 (s, 2H); 3.73 (s, 6H)

Yield: 75 percent.

(b) Production of 3-methoxy-4-thioacetoxy-2E-butenoic acid methyl ester 4.07 g (0.177 mol) of sodium is dissolved in 180 ml of methanol and cooled to 0° C. 13.47 g (0.171 mol) of thioacetic acid is instilled in this solution. Then this solution is mixed at 0° C. with a solution of 29.15 g (0.150 mol) of 3-methoxy-4-chloro-2E-butenoic acid methyl ester in 40 ml of methanol. It is stirred again overnight at room temperature. The precipitated salt is filtered off, the solvent is evaporated on the rotary evaporator and mixed with a little methylene chloride for precipitation of the remaining salt. After filtering off, evaporation of the solvent and drying of the residue in a high vacuum, 36.53 g of a yellow-colored liquid with a content according to GC of 82.8 percent is obtained. This corresponds to 30.25 g of 100 percent product $\hat{=}$98.7 percent yield. Further data concerning the compound is:

$Bp_{0.2}$=95° C.

MNR (CDCl$_3$, 300 MHz) $\delta$=2.36 (s. 3H), 3.66 (s, 3H), 3.71 (s, 3H), 4.29 (s, 2H), 5.10 (s, 1H), MS (70 eV) m/z=204 (M+, 12), 162 (35), 130 (80) 43 (100).

(c) Production of 4-methoxy-2-(5H)-thiophenone 37.77 g (0.145 mol) of 3-methoxy-4-thioacetoxy-2E-butenoic acid methyl ester (82.8 percent) is introduced and mixed with stirring with a solution of 12.20 g (0.217 mol) of KOH in 45 ml of water. After about 30 minutes, a yellowish-colored solid precipitate. This product is filtered by suction and after short drying is recrystallized from 20 ml of methanol. 15.0 g of a white product with a melting point 90° to 91° C. (GS: 97.3 percent) is obtained. This corresponds to a yield of 77.4 percent. Further data concerning the compound is:

NMR (CDCl$_3$, 300 MHz) $\delta$=3.87 (s, 3H), 3.91 (s, 2H), 5.49 (s, 1H)

MS 70 eV m/n=130 (M+, 100), 84 (15), 72 (52), 69 (39), 45 (20).

(d) Production of thiotetronic acid 2.60 g (0.0194 mol) of 4-methoxy-2(5H) thiophenone (97.3 percent) is dissolved in 30 ml of acetic acid and saturated at 40° C. with gaseous hydrochloric acid. The reaction mixture is stirred at this temperature for 16 hours. Then the acetic acid is concentrated under vacuum on the rotary evaporator. The raw product is washed with 10 ml of toluene, filtered by suction and dried in a high vacuum. 2.13 g of almost white crystalline thiotetronic acid with a melting point of 120° C. with a content (NaOH titr.) of 99.5 percent is obtained. This corresponds to 2.12 g of 100 percent product=93.9 percent yield.

EXAMPLE 2

Production of 4-methoxy-2(5H) thiophenone from 4-chloro-3-methoxy-2E-butenoic acid methyl ester and sodium hydrogen sulfide 11.6 g (0.14 mol) of 90 percent sodium hydrogen sulfide monohydrate is dissolved in 90 ml of methanol. A solution of 17.0 g (0.1 mol) of 96.7 percent 4-chloro-3-methoxy-2E-butenoic acid methyl ester in 10 ml of methanol is instilled into this solution at 50° C. in 4 hours. It is stirred for another 2 hours and the methanol is then distilled off under vacuum on the rotary evaporator. The residue is mixed with 100 ml of water and extracted twice with 80 ml each of methylene chloride. The organic phase is dried over sodium sulfate and concentrated by evaporation. The residue is recrystallized hot from 15 ml of ethanol. 5.12 g of yellow-colored product with a melting point of 90° C. is obtained. Further data concerning the compound is: content (GC): 96 percent; yield: 37.8 percent.

EXAMPLE 3

Synthesis of (+)biotin starting with thiotetronic acid (a) 3-Phenylazothiotetronic acid 5.02 g Aniline is added dropwise into 28 ml of a 6N hydrochloric acid solution at 0° C.

To the formed suspension a solution of 3.81 g sodium nitrite in water is added during 30 min. (0° C.). Then, at 5° C. 5.78 g thiotetronic acid solved in 49 ml sodium hydroxide 1N is added with strong stirring during 30 min. At the same time 55 ml of a 1N sodium bicarbonate solution is introduced to keep the pH at 7.0. The yellow product obtained is filtered off, washed with water and dried in vacuo.

Yield: 10.5 g=95 percent 3-phenylazothiotetronic acid m.p. 195° to 196.5° C.

(b) 3-Phenylazo-4-[(R)-(1-phenylethyl amino)]-thien-2-(5H)-one 6.56 g 3-Phenylazothiotetronic acid is solved in 165 ml of toluene under reflux. Then 14.53 g R-1-phenylethyl amine and 2.19 g boron trifluorid ethyl etherate divided in four portions in toluene is added during 40 min.

The reaction mixture is cooled to room temperature and extracted (a) with 100 ml 0.9N HCl (b) with 50 ml of a saturated sodium bicarbonate solution and finally (c) with a saturated sodium sulfate solution.

The dark brown solution is dried with magnesium sulfate and evaporated.

To the brown oily residue ethyl ether is added to crystallize the product. Additional recrystallization with ethyl ether yields 58 percent of the title product. m.p. 129° to 130° C.

(c) 3-Amino-4-[(R)-)1-phenylethyl amino)]-thien-2(5H)-one 0.49 g Platin 5 percent on charcoal is inserted to an autoclave together with a solution of 5 g 3-phenylazo-4-[(R)-(1-phenylethyl amino)]-thien-2(5H)-one in 30 ml of tetrahydrofurane.

After rinsing the autoclave a hydrogen pressure of 30 bar during 45 min. is maintained. The catalyst is then filtered off in an argon atmosphere. To the mother liquor hexane is added until the title product separates as a yellowish oil.

Yield: 2.4 g=65 percent.

(d) (R)-(1-phenylethyl)-1H-thieno[3.4d]imidazol-2.4 (3H,6H)-dione 11.1 ml of an 1.25M phosgen solution in toluene is dissolved in 22 ml of tetrahydrofurane at 0° C. At the same time 3.24 g of 3-amino-4-[(R)-(1-phenylethyl amino)]-thien-2(5H)-one solved in tetrahydrofurane together with a solution of 2.18 g triethyl amine in tetrahydrofurane is added during 3 hours while maintaining a temperature of 5° C. Then 10 ml of an aqueous 5 percent ammonia solution is added. After evaporating the solvent, extracting the aqueous phase with dichlormethane the residue is chromatographed over a silica gel column with ethyl acetate.

Yield: 2.16 g=60 percent of the title product can be obtained. m.p. 218° to 220° C.

(e) 1-[(R)-(1-phenylethyl)]-3-acetyl-1H-thieno[3.4-d]imidazol-2.4(3H,6H)-dione 0.5 g 1-[(R)-(1-phenylethyl)]-1H-thieno[3.4d] imidazol-2.4(3H,6H)-dione is acylated with 20 ml of acetic acid anhydride at 50° C. during 3 hours. After distilling off the solvent, washing the title product with ethyl ether and drying a yield of 0.43 g=73 percent can be obtained. m.p. 187° to 189.5° C.

(f) 3aS, 6aR-1-[(R)-1-phenylethyl]-3-acetyl-dihydro-1H-thieno[3.4d]imidazol-2.4(3H,3aH)-dione 170 mg of (R)-1-(1-phenylethyl)-3-acetyl-1H-thieno[3.4d] imidazol-2.4(3H,6H)-dione dissolved in acetic acid 15 ml is hydrogenated in the presence of 160 mg 5 percent palladium on charcoal catalyst, under 50 bar hydrogen pressure at 65° C. for 30 hours. The catalyst is filtered off and the filtrate is evaporated to dryness. The residue is separated by preparative thin layer chromatography on four silica gel plates with dichloromethane: ethyl acetate 2:1 as eluent. The desired product 3aS, 6aR-1-[(R)-1-phenylethyl]-3-acetyl-dihydro-1H-thieno[3.4d]imidazol-2.4(3H,3aH)-dione is eluted with an Rf value of 0.5. Recrystallisation from isoproponol yielded 18 mg (10 percent yield) of colourless prisms. m.p. 169° to 170° C.

(g) 3aR, 6aS-1-[(R)-1-phenylethyl]-dihydro-1H-thieno[3.4d]imidazol-2.4(3H,6H)-dione 3aR, 6aS-1-[(R)-1-phenylethyl]-3-acetyldihydro-1H-thieno[3.4d]imidazol-2.4(3H,6H)-dione 10.0 g is dissolved in a mixture of acetone 90 ml and in aqueous hydrochloric acid 50 ml, and the solution is refluxed for 24 hours. The acetone is distilled off, the resultant white suspension is cooled to 5° C. overnight and filtered. The preciptate is washed twice with water 50 ml and dried to yield 8.00 g (92 percent yield) of 3 aR, 6aS-1-[(R)-1-phenylethyl]-dihydro-1H-thieno[3.4d]imidazol-2.4(3H,6H)-dione. m.p. 148° to 148.5° C.

(h) 3aR, 6aS-1-[(R)-1-phenylethyl)-3-benzyldihydro-1H-thieno[3.4d]imidazol-2.4(3H,6H)-dione To a solution of 3aR, 6aS-1-[(R)-1-phenylethyl]dihydro-1H-thieno[3.4 d]imidazol-2.4(3H,6H)-dione 32 g and benzylbromide 24.5 g in anhydrous dimethylformamid 300 ml at −10° C. is added sodium hydride (55 percent suspension in oil) 5.75 g, in ten equal portions over a period of 90 minutes. The reaction mixture is stirred for a further two hours at −15° C. and allowed to warm to 0° C. during two hours. Then acetic acid 2 g is added, the solution is evaporated to dryness, xylene 50 ml is added to the residue and the mixture is again evaporated to dryness. The residue is dissolved in a mixture of dichloromethane 50 ml and water 100 ml. The phases are separated and the aqueous phase is further extracted with dichloromethane (3×50 ml). The combined organic phases are dried with anhydrous magnesium sulfate 5 g, filtered and evaporated to dryness. The residue is stirred with methanol 30 ml at 50° C. for 30 minutes, then cooled to 0° C. and filtered to yield 37.5 g (91 percent yield) of 3aR, 6aS-1-[(R)-1-phenylethyl]-3-benzyldihydro-1H-thieno[3.4-d]imidazol-2.4(3H,6H)-dione as white needles. m.p. 148° to 148.5° C.

(i) (3aR, 6aS)-hexahydro-1-[(R)-(1-phenylethyl)]-2-oxo-3-benzylthieno-[3.4d]imidazol-4-ylidenepentane acid 159.8 mg Sodium hydride is suspended in 1.7 ml dimethylsulfoxide and warmed under argon atmosphere to 70° C. The suspension is stirred during 40 minutes until the hydrogen generation stops. The mixture is then cooled to room temperature. Then a solution of 801.5 mg (4-carboxybutyl)-triphenyl-phosponiumbromide in 1 ml dimethylsulfoxide is added. This dark red solution is then introduced to a solution of 271 mg of (3aR, 6aS)-1-[(R)-(1-phenylethyl)]-3-benzyl-dihydro-1H-thieno-[3.4d]imidazol-2.4(3H,6H]-dione in 2 ml dimethylsulfoxide and 0.2 ml toluene and stirred during 2 hours at room temperature. Then 1 g of ice, 1 ml of conc. HCl and additional 9 g ice is added. 5 minutes afterwards 5 ml water, 10 ml benzene and 5 ml ethylacetate is added. The mixture is again stirred over 60 minutes. The resulting two phases are then separated, whereby the organic layer is dried over magnesium sulfate and then applied on 4 preparative silica gel thin layer chromatography plates. The title product was obtained by eluation with ethylacetate.

Yield: 38.2 mg=12 percent (colorless oil).

(j) (3aR, 6aS) hexahydro-1-[(R)-(1-phenylethyl)]-2-oxo-3-benzyl-thieno-[3.4d]imidazol-pentan aicd In an autoclave 78.6 mg of the product of process (i) dissolved in 5 ml isopropylalcohol is added to 39 mg palladium 5 percent on charcoal. After rinsing the autoclave twice with hydrogen the mixture is hydrogenated at 50 bar pressure at 50° C. during 24 hours. The catalyst is then filtered off and the solvent is evaporated. The residue as colorless oil corresponds to the title product.

Yield: 56.1 mg=72 percent.

(k) (+)Biotin

A solution of the product of process (j) dissolved in 4 ml hydroboric acid (48 percent) is stirred during 3 hours at 120° C. under reduced pressure of 400 m bar. After cooling the reaction mixture is extracted with 5 ml of toluene. The aqueous layer is evaporated to dryness. The residue is again dissolved in 10 ml water and then extracted with 10 ml chloroform at 60° C. The aqueous layer is distilled off to 1 ml and cooled. d-(+)Biotin crystallized in the form of yellowish crystals.

Yield: 40 mg=72 percent. m.p. 227° to 229° C.

$[\alpha]_D^{25}[c=0.1N\ NaOH]+84.5°\ C.$

What is claimed is:

1. Process for the production of a 4-alkoxy-2(5H) thiophenone of the formula:

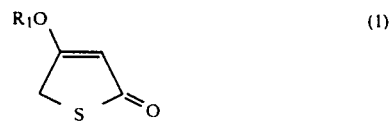

(1)

wherein $R_1$ is a straight-chain or branched alkyl having 1 to 4 carbon atoms, comprising reacting a 3-alkoxy-4-halo-2E-butenoic acid alkyl ester of the formula:

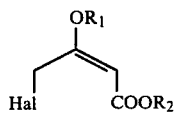 (2)

wherein $R_1$ and $R_2$ each is the same or different straight-chain or branched alkyl having 1 to 4 carbon atoms and Hal is chlorine or bromine, either (a) with an alkali salt of thioacetic acid to a 3-alkoxy-4-thioacetoxy-2E-butenoic acid alkyl ester, isolating the 3-alkoxy-4-thioacetoxy-2E-butenoic acid alkyl ester and further converting the 3-alkoxy-4-thioacetoxy-2E-butenoic acid alkyl ester with an alkali hydroxide to the 4-alkoxy-2(5H) thiophenone or (b) directlywith an alkali hydrogen sulfide to the 4 alkoxy-2(5H) thiophenone.

2. Process according to claim 1 wherein the 3-alkoxy-4-halo-2E-butenoic acid alkyl ester is produced in a known way, starting from a 4-haloacetoacetic acid alkyl ester by reaction with orthoformic acid trialkyl ester.

3. Process according to claim 2 wherein the alkali salt of thioacetic acid is sodium thioacetate.

4. Process according to claim 3 wherein the alkali hydrogen sulfide is sodium hydroge sulfide.

5. Process according to claim 4 wherein the reaction with the alkali salt of thioacetic acid or the reaction with the alkali hydrogen sulfide takes place in the presence of a lower aliphatic alcohol as a solvent.

6. Process according to claim 5 wherein the reaction with the alkali salt of the thioacetic acid takes place at a temperature between 20° and 60° C.

7. Process according to claim 6 wherein the reaction with the alkali hydroxide takes place in the presence of water.

8. Process according to claim 7 wherein the direct reaction with the alkali hydrogen sulfide takes place at a temperature between 20° and 70° C.

9. Process according to claim 1 wherein the alkali salt of thioacetic acid is sodium thioacetate.

10. Process according to claim 1 wherein the alkali hydrogen sulfide is sodium hydrogen sulfide.

11. Process according to claim 1 wherein the reaction with the alkali salt of thioacetic acid or the reaction with the alkali hydrogen sulfide takes place in the presence of a lower aliphatic alcohol as a solvent.

12. Process according to claim 1 wherein the reaction with the alkali salt of the thioacetic acid takes place at a temperature between 20° and 60° C.

13. Process according to claim 1 wherein the reaction with the alkali hydroxide takes place in the presence of water.

14. Process according to claim 1 wherein the direct reaction with the alkali hydrogen sulfide takes place at a temperature between 20° and 70° C.

15. Process according to claim 1 wherein the 3-alkoxy-4-halo-2E-butenoic acid alkyl ester is reacted with the alkali salt of thioacetic acid to the 3-alkoxy-4-thioacetoxy-2E-butenoic acid alkyl ester, isolating the 3-alkoxy-4-thioacetoxy-2E-butenoic acid alkyl ester, and converting the 3-alkoxy-4-thioacetoxy-2E-butenoic acid alkyl ester with the alkali hydroxide to the 4-alkyoxy-2(5H) thiophenone.

16. Process according to claim 1 wherein the 3-alkoxy-4-halo-2E-butenoic acid alkyl ester is directly reacted with the alkali hydrogen sulfide to the 4-alkoxy-2(5H) thiophenone.

* * * * *